United States Patent
Wan et al.

(10) Patent No.: US 8,556,826 B2
(45) Date of Patent: Oct. 15, 2013

(54) FECAL SPECIMEN COLLECTOR

(76) Inventors: John Wan, San Marino, CA (US);
Zhijing Wan, Beijing (CN)

(*) Notice: Subject to any disclaimer, the term of this patent is extended or adjusted under 35 U.S.C. 154(b) by 467 days.

(21) Appl. No.: 12/145,957

(22) Filed: Jun. 25, 2008

(65) Prior Publication Data
US 2009/0005705 A1    Jan. 1, 2009

(30) Foreign Application Priority Data
Jun. 28, 2007    (CN) .................. 2007 2 0151448 U

(51) Int. Cl.
*A61B 10/00*    (2006.01)
(52) U.S. Cl.
USPC .......... 600/569; 604/317; 73/863; 73/863.21; 73/864; 73/864.91
(58) Field of Classification Search
USPC .......... 600/562, 569; 422/102, 104, 292, 296; 604/317, 405–406; 73/863.21, 864.91, 73/863, 864
See application file for complete search history.

(56) References Cited

U.S. PATENT DOCUMENTS

| 3,083,145 A * | 3/1963 | Ryan ..................... 435/288.2 |
|---|---|---|
| 3,390,759 A * | 7/1968 | Vanderbeck ................ 206/216 |
| 3,966,552 A * | 6/1976 | Pagano et al. ............. 435/288.1 |
| 5,514,341 A * | 5/1996 | Urata et al. .................. 422/534 |
| 5,890,828 A * | 4/1999 | Gueret ........................ 401/126 |
| 6,207,113 B1 * | 3/2001 | Kagaya ....................... 422/534 |
| 6,780,160 B2 | 8/2004 | Zhou et al. |
| 6,921,370 B2 | 7/2005 | Zhou et al. |
| 7,048,693 B2 | 5/2006 | Zhou et al. |
| 7,163,514 B2 | 1/2007 | Zhou et al. |
| 2004/0184966 A1 * | 9/2004 | Zhou et al. ................... 422/102 |
| 2007/0275475 A1 * | 11/2007 | Liang ........................... 436/165 |

FOREIGN PATENT DOCUMENTS

JP    2004317481 A * 11/2004

* cited by examiner

*Primary Examiner* — Rene Towa
(74) *Attorney, Agent, or Firm* — Scully, Scott, Murphy & Presser, P.C.

(57) ABSTRACT

The present invention provides a fecal specimen collector. The fecal specimen collector consisting of a top cover, a bottle body, a specimen output end and a bottom cover, wherein a lower portion of the top cover forms a sampling end which may be inserted into the bottle body through an upper end of the bottle body, the top cover is connected with the upper end of the bottle body, the specimen output end is hermetically coupled with a lower portion of the bottle body, and the bottom cover surrounds the specimen output end and couples to the bottle body, wherein a convex is formed on the inner center of the bottom cover, and is inserted into a specimen output port of the specimen output end. The fecal specimen collector according to the present application has a small and delicate structure which has the advantages of easy operation, convenient portability and pollution free, etc.

13 Claims, 3 Drawing Sheets

FECAL SPECIMEN COLLECTOR

BACKGROUND OF THE INVENTION

1. Field of the Invention

The present invention relates to a medical appliance, and more particularly, to a device for collecting a specimen of fecal matter.

2. Background

The analysis of feces has become a means for diagnosing diseases commonly employed by the medical units due to its special meaning on diagnosing certain diseases. The common methods for examining feces include a visual check, a microscopic examination, and a chemical examination and so on.

The method of collecting the specimen of fecal matter directly affects the accuracy of the examination. However, the current common methods for collecting the specimen are not precise. The US patent No. 20060210448 discloses a fecal specimen collection device, in which a fecal specimen collecting portion is a plastic stick so that the specimen amount is small and the fluid feces can not be received easily. In addition, the specimen output port of the device of the above patent has to be broken off with fingers and thumb, which can not be done easily, and the liquid in the vessel can easily spray.

Most of the fecal specimen devices that can be found on the market are usually simple and crude, which often causes much inconvenience to those who carry out the operation of collecting the fecal specimen and those who carry out the operation of taking out the fecal specimen in order for examination since the odor smell and the pollution to examination environment can not be prevented.

SUMMARY OF THE INVENTION

In order to solve the above technical problems, the present invention is to provide a fecal specimen collector having a simple and delicate structure, which has the advantages of easy operation, convenient portability and pollution free, etc.

The present invention provides a fecal specimen collector consisting of a top cover, a bottle body, a specimen output end and a bottom cover, wherein a lower portion of the top cover forms a sampling end which may be inserted into the bottle body through a upper end of the bottle body, the top cover is connected with the upper end of the bottle body, the specimen output end is hermetically coupled with a lower portion of the bottle body, and the bottom cover surrounds the specimen output end and couples to the bottle body, wherein a convex is formed on the inner center of the bottom cover and inserted into a specimen output port of the specimen output end.

When the bottle body and the bottom cover are sealed by screwing, the convex inside the bottom cover just seals the specimen output port to prevent the liquid in the bottle body from leaking out. The sampling end has a brush structure to ensure that adequate amount of sample may be collected once during the operation.

According to one aspect of the present invention, the spacing septum is formed inside the bottle body for dividing the inner space of the bottle body into a first and second chambers, and the spacing septum is formed with a through hole at the center thereof so that the sampling end enters into the second chamber through the through hole and seals the hole when it is inserted into the bottle body.

According to one aspect of the present invention, the sampling end comprises a brush structure, or has a stick shape with a plurality of sheets protruding from its stick.

According to one aspect of the present invention, the bottle body is a hollow tube, the inner surface of the upper end of which is disposed with an internal thread structure, and the handle end has a corresponding external thread structure.

According to one aspect of the present invention, the top cover includes a handle end, a sampling end and a round plate protruding from a connection part between the handling end and the sampling end.

According to one aspect of the present invention, the inner surface of the upper end of the bottle body is disposed with an external thread structure, and the handle end has a corresponding internal thread structure.

According to one aspect of the present invention, the first chamber is formed of transparent material, and the second chamber is used for preserving diluent liquid.

According to one aspect of the present invention, the specimen output end has an upper and lower communicating structure, one end of which is a specimen output port into which the convex is inserted, and the other end of which is coupled to the bottle body by interference fit, wherein the specimen output end is coupled with the bottle body by being inserted therein, a sealing groove is disposed at a position of the specimen output end where the bottle body is coupled, and a sealing ring is disposed in the sealing groove.

According to one aspect of the present invention, the spacing septum is disposed with a sealing ring on a surface thereof facing the first chamber, and when the sampling end is inserted into the bottle body, the sealing ring is interposed between the round plate and the spacing face.

DETAILED DESCRIPTION OF EXEMPLARY EMBODIMENTS OF THE PRESENT INVENTION

The First Embodiment

Figure 1:
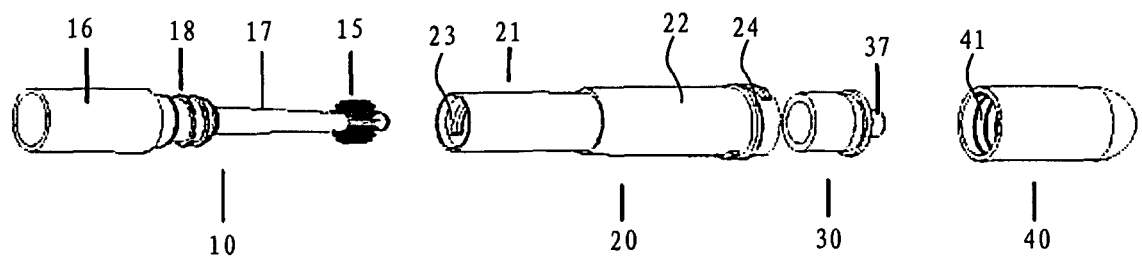
FIG. 1 is an exploded perspective view of the fecal specimen collector according to the first embodiment of the present invention.
Figure 2:
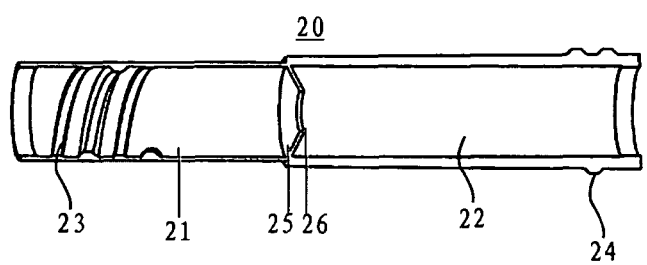
FIG. 2 is a cross section view of the bottle body of the fecal specimen collector according to the first embodiment of the present invention.
Figure 3:
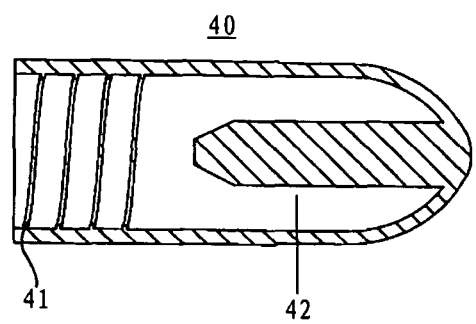
FIG. 3 is a cross section view of the bottom cover of the fecal specimen collector according to the first embodiment of the present invention.

FIG. 1 is an exploded perspective view of the fecal specimen collector according to the first embodiment of the present invention. As shown in FIG. 1, the fecal specimen collector comprises a hollow bottle body 20 with openings at both ends thereof, a top cover 10 coupled with one of the opening of the bottle body 20 at one end, a specimen output end 30 coupled with the other opening of the bottle body 20 at the other end, and a bottom cover 40 coupled with the specimen output end 30.

The top cover 10 is formed with a handle 16 at the upper end thereof, and a sampling end 15 at the lower end thereof. The sampling end 15 can be inserted into the bottle body 20 from the upper end of the bottle body 20. The specimen output end 30 is inserted into the opening at the lower end of the bottle body 20 so as to achieve an interference fit between the specimen output end 30 and the lower portion of the bottle body 20, and the bottom cover 40 is coupled to the bottle body 20 by screwing.

The sampling end has a brush structure to collect adequate amount of sample once during the operation.

The top cover 10 further comprises a stick 17 connected between the handle 16 and the sampling end 15, wherein an external thread portion 18 is formed between the handle 16 and the stick 17.

The bottle body 20 is a hollow tube, disposed with an internal thread portion 23 on an inner surface of the upper end, which is to be coupled to the external thread portion 18 of the top cover 10. The inside of the bottle body 20 has a spacing septum 25 dividing the inner space of the bottle body 20 into two chambers: an observing chamber 21 between the spacing septum 25 and the internal thread portion 23, which is formed of a transparent material so as to form a transparent observing window; and a liquid storing chamber 22 between the spacing septum 25 and the lower end of the bottle body 20 for preserving the diluent for diluting the specimen of fecal matter. The spacing septum 25 is disposed with a through hole 26 at the center thereof. When the sampling end 15 is inserted into the bottle body 20, it goes into the liquid storing chamber 22 by passing through the hole 26. The upper and lower end of the specimen output end 30 are communicated with each other, one of which having a larger diameter, and is connected with the bottle body 20 to be communicated with the inner space thereof, and the other one of which has a smaller diameters, and forms a liquid discharging passage. The end having a smaller diameter is referred to as a specimen output port 37.

The bottom cover 40 has a cavity with an opening at one end. The opening has an internal thread 41 coupled to an external thread 24 on the lower end of the bottle body 20. The bottle body 20 contains the diluent therein and the top cover 10 and the bottom cover 40 are sealed from all directions to prevent the diluent from leaking out.

The bottom cover 40 is formed with a convex 42 at the inner bottom center thereof. When the bottle body 20 and the bottom cover 40 are threaded-coupling, the convex 42 on the inner bottom center of the bottom cover 40 is inserted into the specimen output port 37 to seal the passage for preventing the liquid in the bottle body from leaking out.

When sampling, the user first loosens the upper cover 10 so as to take out the upper cover 10. Then the user inserts the sampling end 15 of the upper cover 10 into the specimen of fecal matter so as to dip a portion of the specimen, puts the sampling end 15 dipping with the specimen into the bottle body 20 again. At this time, most of the specimen will be blocked by the spacing septum 25 so that the form and shape of the feces sample can be observed through the observing window. After that, the user tightly screws the top cover 10 and shakes the bottle body 20 to flush the feces sample away from the sampling end 15 by the diluent in the liquid storing chamber 22 and make it uniform. At last, the checker screws off the bottom cover 40 so that the sample can drop from the specimen output port 37 of the bottle body 20 for the microscopic examination or the test paper examination. When only one of the top cover 10 and the bottom cover 40 is opened, the liquid would not automatically flow out due to the negative pressure principle. That is, the liquid would not flow out until the outside of the bottle body 20 is pressed and the specimen output end 30 is downward.

The Second Embodiment

Figure 4:
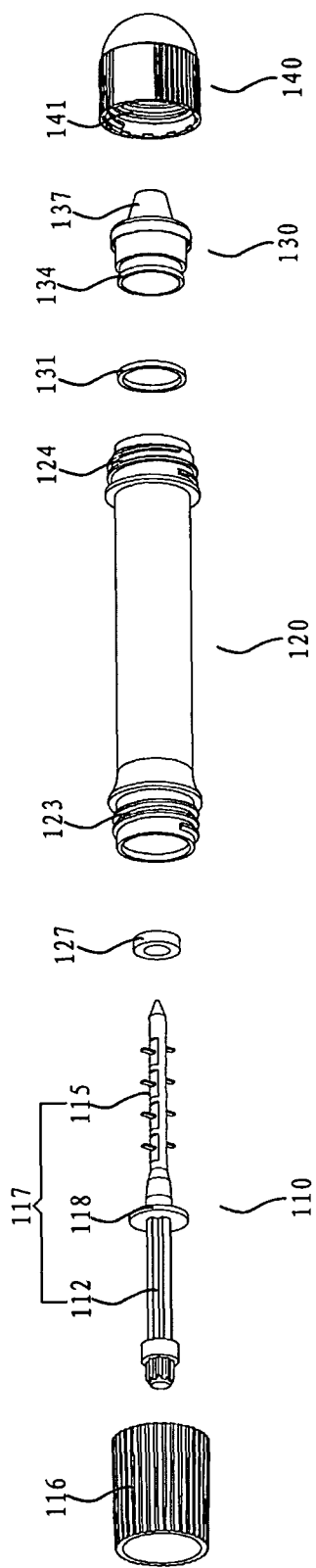
FIG. 4 is an exploded perspective view of the fecal specimen collector according to the second embodiment of the present invention.
Figure 5:
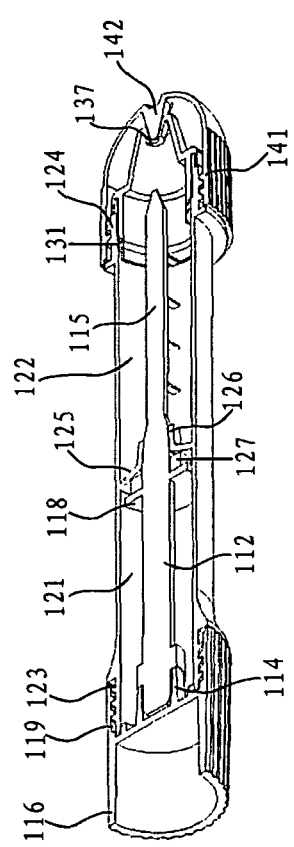
FIG. 5 is a general cross section view of the fecal specimen collector according to the second embodiment of the present invention.

FIG. 4 is an exploded perspective view of the fecal specimen collector according to the second embodiment of the present invention. FIG. 5 is a general cross section view of the fecal specimen collector according to the second embodiment of the present invention.

The fecal specimen collector according to the second embodiment further includes sealing rings 127 and 131 on the basis of the first embodiment so as to secure the sealing of the bottle body. Meanwhile, the sampling end uses sheets instead of hair brush.

As shown in the drawings, the fecal specimen collector according to the second embodiment comprises a hollow bottle body 120 with openings at both ends thereof, an top cover 110 coupled with one of the opening of the bottle body 120 at one end, a specimen output end 130 coupled with the other opening of the bottle body 120 at the other end, and a bottom cover 140 coupled with the specimen output end 130.

The top cover 110 is formed with two parts coupled with each other including a handle 116 and a sampling stick 117. The sampling stick 117 comprises a connection rod 112, a sampling end 115 and a round plate 118 protruding from a connection portion between the connection rod 112 and the sampling end 115. One end of the connecting rod 112 is coupled with the handle 116. The sampling end 115 has a stick structure having sheets protruding from its stick so as to ensure adequate amount of sample to be collected once during the operation. The sampling end 115 can be inserted into the bottle body 120 from the upper end of the bottle body 120.

The handle 116 generally has a shape of cylinder, and has a protruding cylinder structure 114 therein which is connected with one end of the connection rod 112. The outer cylinder structure of the handle 116 has an internal screw 119, which is coupled to a corresponding external screw 123 on the bottle body 120.

The bottle body 120 is a hollow tube, disposed with an external screw 123 on an inner surface of the upper end thereof, which is to be coupled to the internal screw 119 of the top cover 110. The inside of the bottle body 20 has a spacing septum 125 dividing the inner space of the bottle body 120 into two chambers: an observing chamber 121 between the spacing septum 125 and the external screw 123, which is formed of a transparent material so as to form a transparent observing window; and a liquid storing chamber 122 between the spacing septum 125 and the lower end of the bottle body 210 for preserving the diluent for diluting the specimen of fecal matter. The spacing septum 125 is disposed with a through hole 126 at the center thereof. When the sampling end 115 is inserted into the bottle body 120, it goes into the liquid storing chamber 122 by passing through the hole 126. The upper and lower end of the specimen output end 130 are communicated with each other, one which has a larger diameters, is connected with the bottle body 120 and communicated with its inner space, and the other one which has a smaller diameters, and forms a liquid discharging passage. The end having a smaller diameter is referred to as the specimen output port 137.

The spacing septum 125 is disposed with a sealing ring 127 thereon. When the top cover 110 and the bottle body 120 are closely connected with each other, the round plate 118, the sealing ring 127 and the spacing septum 125 are closely disposed in sequence, which may prevent the diluent liquid contained between the spacing septum 125 and the specimen output end 130 from leaking into the observing chamber 121.

The specimen output end 130 and the bottle body 120 are coupled with each other by inference fit with the specimen output end 130 being inserted into the lower end of the bottle body 120. An sealing groove 134 is formed on the outer circumference of the specimen output end 130, and the sealing ring 131 is disposed therein so that the sealing between the specimen output end 130 and the bottle body 120 can be ensured to prevent the diluent in the bottle body 120 from flowing out from a connecting part between the specimen output end 130 and the bottle body 120.

The bottom cover 140 has a cavity with an opening at one end. The opening has an internal thread 141 coupled to an external screw 124 on the lower end of the bottle body 120. The bottom cover 140 is coupled to the bottle body by threading.

The bottom cover 140 is formed with a convex 142 at the inner bottom center thereof. When the bottle body 120 and the bottom cover 140 are threaded-coupling, the convex 42 on the bottom center of the bottom cover 40 is inserted into the specimen output port 37 to seal the passage for preventing the liquid in the bottle body from leaking out.

When sampling, the user first looses the upper cover 110 is so as to take out the upper cover 110. Then the user inserts the sampling end 115 and the round plate 118 of the upper cover 110 into the specimen of fecal matter so as to dip a portion of the specimen. After that, the sampling end 115 dipping with the specimen is put into the bottle body 120 again. At this time, a part of the specimen will be blocked on the round plate 118 so that the form and shape of the feces sample can be observed through the observing window. Then, the user tightly screws the top cover 10 and shakes the bottle body 120 to flush the feces sample away from the sampling end 115 by the diluent in bottle body 120 and make it uniform. At last, the checker screws off the bottom cover 40 so that the sample can drop from the specimen output port 37 of the bottle body 120 for the microscopic examination or the test paper examination. When only one of the top cover 10 and the bottom cover 40 is opened, the liquid would not automatically flow out due to the negative pressure principle. That is, the liquid would not flow out until the outside of the bottle body 120 is pressed and the specimen output end 130 is downward.

Although the fecal specimen collector in the embodiment is explained to include the bottle body and the specimen output end provided separately, obviously, the bottle body and the specimen output end can be formed integrally.

With the fecal specimen collector according to the present invention, no spray of the fecal specimen diluent will occur when the checker take the diluent for examination so that the pollution is prevented and the operation is convenient.

Furthermore, a sealing ring is disposed on the spacing septum in order to prevent the diluent from leaking into the observing window from the through hole of the spacing septum, thereby preventing it from leaking outward at the handle. In addition, another sealing ring is disposed at the connecting portion between the specimen output end and the bottle body in order to prevent the dulient from leaking out at the same portion.

In summary, compared with the prior art, the fecal specimen collector provided in the present invention has the following advantageous:

(1) it has a sealed structure, no diluent leaking out and no abnormal smell spreading, which are safe and clean;

(2) it has a simple structure and a convenient portability, which is adapted to collect samples at various sites;

(3) it has a large amount of sampling, which is adapted to collect fecal specimen in various forms;

(4) it has a wide applications, e.g. the spacing septum ensures a proper amount of fecal specimen to be solved in the diluent for generating a sample liquid, which drops from the specimen output port suit for test paper examination or microscopic examination, when the collector is used; and another portion of the fecal specimen blocked by the spacing septum is piled up thereon so that the feces sample can be observed by naked eyes from the observing window and a primary diagnoses can be made according to the color and shape of the sample.

While the present invention has been shown and described with reference to certain exemplary embodiments thereof, it will be understood by those skilled in the art that various changes in form and details may be made therein without departing from the spirit and scope of the invention as defined by the appended claims.

What is claimed is:

1. A fecal specimen collector comprising:
   a top cover comprising a sampling stick, the sampling stick comprising a plate and an elongated sampling end extending downwardly from the plate;
   a bottle body into which the sampling stick is inserted;
   a sealing ring and a spacing septum disposed within the bottle body, the sealing ring and the spacing septum dividing the bottle body into a first chamber and a second chamber, the second chamber containing diluent liquid;
   a specimen output end having a fluid passageway in fluid communication with the second chamber of the bottle body, the specimen output end further having an orifice at the bottom wall of the specimen output end through which the diluent liquid is discharged;
   a bottom cover comprising a convex being configured to engage the orifice of the specimen output end for preventing the diluent liquid from discharging upon being pressed; and
   a through hole formed in the spacing septum and the sealing ring, through which the elongated sampling end of the top cover is inserted to sealingly engage the plate with the sealing ring;
   wherein the orifice is configured to have a sufficiently small dimension, wherein when the convex is disengaged from the orifice and the orifice is positioned downwardly, the diluents liquid is not discharged unless the bottle body is pressed.

2. The fecal specimen collector of claim 1, wherein the elongated sampling end comprises a brush structure.

3. The fecal specimen collector of claim 1, wherein the elongated sampling end comprises a stick and includes a plurality of sheets protruding from the stick.

4. The fecal specimen collector of claim 1, wherein the top cover comprises a handle from which the sampling stick extends, and the sampling stick further comprises a connection rod for connecting the handle to the plate.

5. The fecal specimen collector of claim 1, wherein the bottle body comprises a hollow tube having a top end and a bottom end, the top end being provided with an internal screw structure, and the top cover comprises an external screw structure for operatively engaging the internal screw structure.

6. The fecal specimen collector of claim 1, wherein the bottle body comprises a hollow tube having a top end and a bottom end, the top end being provided with an external screw structure, and the top cover comprises an internal screw structure for operatively engaging the external screw structure.

7. The fecal specimen collector of claim 1, wherein the specimen output end is coupled to the bottle body by interference fit.

8. The fecal specimen collector of claim 1, wherein the specimen output end comprises a sealing groove and a secondary sealing ring disposed within the sealing groove.

9. The fecal specimen collector of claim 1, wherein the convex has a taper shape.

10. The fecal specimen collector of claim 1, wherein the lower surface of the round plate which contacts the sealing ring is flat, and the upper surface of the sealing ring which contacts the lower surface of the round plate is flat.

11. The fecal specimen collector of claim 2, wherein the brush structure has a diameter greater than the diameter of the through hole of the spacing septum.

12. The fecal specimen collector of claim 3, wherein the plurality of sheets have a diameter greater than the diameter of the through hole of the spacing septum.

13. The fecal specimen collector of claim 1, wherein the sealing ring has a diameter smaller than the diameter of the spacing septum.

* * * * *